(12) United States Patent
Metral et al.

(10) Patent No.: US 9,006,312 B2
(45) Date of Patent: Apr. 14, 2015

(54) COMPOSITE COMPOSITIONS

(75) Inventors: Guillaume Metral, Frankfurt (DE); Bernd Hoevel, Sinzheim (DE); Joseph Gan, Strasbourg (FR); Michael J. Mullins, Houston, TX (US)

(73) Assignee: Dow Global Technologies LLC, Midland, MI (US)

( * ) Notice: Subject to any disclaimer, the term of this patent is extended or adjusted under 35 U.S.C. 154(b) by 190 days.

(21) Appl. No.: 13/513,205

(22) PCT Filed: Nov. 10, 2010

(86) PCT No.: PCT/US2010/056101
§ 371 (c)(1),
(2), (4) Date: Jun. 1, 2012

(87) PCT Pub. No.: WO2011/068643
PCT Pub. Date: Jun. 9, 2011

(65) Prior Publication Data
US 2012/0289624 A1  Nov. 15, 2012

Related U.S. Application Data

(60) Provisional application No. 61/265,807, filed on Dec. 2, 2009.

(51) Int. Cl.
| | |
|---|---|
| B32B 15/092 | (2006.01) |
| B32B 27/04 | (2006.01) |
| B32B 27/38 | (2006.01) |
| C08G 59/24 | (2006.01) |
| C08G 59/50 | (2006.01) |
| C08G 59/68 | (2006.01) |
| C08K 7/02 | (2006.01) |
| C08K 7/14 | (2006.01) |
| C08K 3/40 | (2006.01) |
| C08L 63/00 | (2006.01) |
| C08L 63/02 | (2006.01) |
| H01L 33/56 | (2010.01) |
| H05K 7/02 | (2006.01) |
| C08G 59/40 | (2006.01) |
| C08K 3/00 | (2006.01) |
| C08G 59/06 | (2006.01) |
| C08G 59/22 | (2006.01) |
| C07D 301/28 | (2006.01) |

(52) U.S. Cl.
CPC ............ C08G 59/245 (2013.01); B32B 15/092 (2013.01); B32B 27/04 (2013.01); B32B 27/38 (2013.01); C07D 301/28 (2013.01); C08G 59/24 (2013.01); C08G 59/4021 (2013.01); C08G 59/686 (2013.01); C08K 3/0033 (2013.01); C08K 7/02 (2013.01); C08K 7/14 (2013.01); H01L 33/56 (2013.01); H05K 7/02 (2013.01); C08L 63/00 (2013.01); C08G 59/066 (2013.01); C08G 59/22 (2013.01)

(58) Field of Classification Search
None
See application file for complete search history.

(56) References Cited

U.S. PATENT DOCUMENTS

| | | | |
|---|---|---|---|
| 3,018,262 A | 1/1962 | Schroeder | |
| 3,422,065 A | 1/1969 | Wulff et al. | |
| 4,438,241 A * | 3/1984 | Mark et al. | 525/444 |
| 4,638,027 A | 1/1987 | Mark et al. | |
| 4,925,901 A | 5/1990 | Bertram et al. | |
| 5,126,428 A | 6/1992 | Freitag et al. | |
| 5,369,192 A | 11/1994 | Ko et al. | |
| 5,376,453 A | 12/1994 | von Gentzkow et al. | |
| 5,401,814 A | 3/1995 | Shomaker et al. | |
| 5,405,688 A | 4/1995 | Decker et al. | |
| 5,698,600 A | 12/1997 | Wulff et al. | |
| 5,736,620 A | 4/1998 | Earls et al. | |
| 6,063,876 A | 5/2000 | Hayakawa et al. | |
| 6,153,719 A | 11/2000 | Abbey et al. | |
| 6,242,083 B1 | 6/2001 | McGrail et al. | |
| 6,403,220 B1 | 6/2002 | Brennan | |
| 6,572,971 B2 | 6/2003 | Martin | |
| 6,613,839 B1 * | 9/2003 | Gan et al. | 525/117 |
| 6,632,893 B2 | 10/2003 | Konarski et al. | |
| 6,887,574 B2 | 5/2005 | Dean et al. | |
| 7,037,958 B1 | 5/2006 | Hansen et al. | |
| 7,163,973 B2 | 1/2007 | Ahsan | |
| 7,582,706 B2 | 9/2009 | Groppel | |
| 8,937,114 B2 * | 1/2015 | Metral et al. | 523/400 |
| 2002/0119317 A1 | 8/2002 | Gan et al. | |
| 2005/0171237 A1 | 8/2005 | Patel et al. | |

(Continued)

FOREIGN PATENT DOCUMENTS

| | | |
|---|---|---|
| CN | 1171219 | 5/2005 |
| CN | 101519492 | 9/2009 |

(Continued)

OTHER PUBLICATIONS

Derwent accession No. 2005-768434 for Chinese Patent No. 1,771,219 A, May 10, 2006 and WO 2005/092826 A1, Oct. 6, 2005, Akutsu et al., three pages.*

(Continued)

Primary Examiner — Robert Sellers
(74) Attorney, Agent, or Firm — Brooks, Cameron & Huebsch, PLLC

(57) ABSTRACT

A curable resin composition for composites and electrical laminates including (I) at least one thermoset resin composition; (II) at least one hardener; and (III) at least one reinforcing material; wherein the composite or electrical laminate has a balance of properties including a combination of (a) a Tg of at least about 150° C.; and (b) a water uptake of less than about 2.5 wt %.

17 Claims, No Drawings

(56) References Cited

U.S. PATENT DOCUMENTS

| | | |
|---|---|---|
| 2006/0293172 A1 | 12/2006 | Rubinsztajn et al. |
| 2007/0221890 A1 | 9/2007 | Gan |
| 2012/0238668 A1* | 9/2012 | Metral et al. .................. 523/427 |
| 2012/0238709 A1* | 9/2012 | Metral et al. .................. 525/523 |

FOREIGN PATENT DOCUMENTS

| | | |
|---|---|---|
| EP | 0274209 | 7/1988 |
| EP | 2070962 | 6/2009 |
| GB | 1409835 | 10/1975 |
| JP | 2006-259249 A * | 9/2006 |
| WO | 9900451 | 1/1999 |
| WO | 0125358 | 4/2001 |
| WO | 2005092826 | 10/2005 |
| WO | WO 2005/092826 A1 * | 10/2005 |
| WO | 2005118604 | 12/2005 |
| WO | 2006052727 | 5/2006 |
| WO | 2009045835 | 4/2009 |
| WO | 2009058715 | 5/2009 |
| WO | 2009114465 | 9/2009 |
| WO | 2011068644 | 6/2011 |

OTHER PUBLICATIONS

International Search Report and Written Opinion from related PCT application PCT/US2010/056101 dated Jun. 29, 2011, 11 pages.
Lee, et al. "Handbook of Epoxy Resins", McGraw-Hill Book Company, New York, 1967, Chapter 2, 2-1 to 2-33.
L.R. Whittington, "Thermosetting Plastics (thermosets)", Whittington's Dictionary of Plastics, 1978, p. 314.
International Preliminary Report on Patentability from related PCT application PCT/US2010/056101 dated Jun. 14, 2012, 7 pages.
Ullman's Encyclopedia of Industrial Chemistry, 5th Edition, vol. A9, "Dithiocarbamic Acid to Ethanol," 1987, pp. 547-563.

* cited by examiner

COMPOSITE COMPOSITIONS

This application is a National Stage application under 35 U.S.C. 371 of PCT/US2010/056101, filed on Nov. 10, 2010 and published as WO2011/068643 A2 on Jun. 9, 2011, and re-published as WO2011/068643 A3 on Jun. 9, 2011, which claims the benefit of U.S. Provisional Application Ser. No. 61/265,807 filed Dec. 2, 2009, the entire contents of which are incorporated herein by reference in its entirety.

BACKGROUND OF THE INVENTION

1. Field of the Invention

The present invention relates to thermosettable compositions for composites, and more specifically, the present invention relates to thermosettable compositions for composites and electrical laminates; and the composites and electrical laminates made from the thermosettable compositions.

2. Description of Background and Related Art

For electrical laminates and composites, thermosets that do not change properties with changing environmental conditions, such as humidity and temperature, are very desirable. Three desirable properties for aryl glycidyl ethers for these applications are high glass transition temperature (Tg greater than 190° C. by dynamic mechanical thermal analysis with dicyandiamide cure), low monomer viscosity (less than 200 mPa-s at 150° C.), and high epoxy equivalent weight. Epoxies of the present invention exhibit viscosities as low as 120 mPa-s and the dicyandiamide-cured thermosets have Tgs up to 202° C. and EEWs (epoxy equivalent weights) of greater than 190 grams/equivalent (g/eq).

High Tgs are needed for applications where the composite will be exposed to high temperature, for example in a printed circuit board that cycles between ambient and high temperature many times during its lifetime. The properties of the composite degrade precipitously above the temperature of the Tg, and in general high Tg's offer a wide range of use temperature.

A variety of methods are used to prepare composites, and low viscosity resins are typically a necessity. For example, a common process for composite part fabrication is to enfuse a mold that contains a fiber preform. If the resin viscosity is too high the fiber perform will be deformed. Low viscosity has other benefits. For example, adhesion to fiber is usually better for low viscosity resins because wetting is improved and the resin can intercalate into fiber bundles.

Finally, epoxy resins with high EEWs give thermosets with a relatively low concentration of hydroxyls in the backbone. Hydroxyls are formed during typically curing reactions of epoxy resins, such as with dicyandiamide, a multifunctional amine. There is a direct relationship between hydroxyl concentration in a thermoset and water absorption. High water absorption is undesirable in especially in electrical laminates because the properties such as dielectric performance, change with changing humidity.

There are many aryl glycidyl ethers that achieve these properties individually, but not that meet them all properties simultaneously. This balance of properties is difficult to achieve. For example, one common strategy for high Tg is to use polyglycidyl ethers of highly functional polyphenols, especially phenol formaldehyde novolacs which are known as epoxy novolacs. However, examples of such novolacs that have viscosities of less than 200 mPa-s are not capable of achieving high Tgs comparable to the epoxy resins of the present invention. For example, D.E.N.™ 438, an industry standard epoxy novolac, has a viscosity of <200 mPa-s but the Tg of the dicyandiamide-cured thermoset is only 173° C.

Accordingly, there is still a need in the industry to develop new thermoset resins useful for coatings that are difunctional and provide thermosets with a balance of properties including high Tg (>150° C.), low monomer viscosity (<150 mPa-s at 150° C.) and high EEW (>190 g/eq).

SUMMARY OF THE INVENTION

The present invention meets the goal of developing formulations useful for laminates and composites that exhibit toughness, high Tg (>190° C. can be achieved with dicyandiamide cure), and are derived from a low viscosity, (<150 mPa-s at 150° C.), high EEW (>190 g/eq) resin. This has been accomplished through the use of resins and hardeners that contain cycloalkanes in the backbone. These resins are described in Formulas I and II and by the phenolic hardener described in Formula III. Laminates and composites of the present invention can provide low water absorption. For example, when using dicyandiamide (dicy) as a hardener, laminates can be prepared that absorb less than 2.5 wt % water (expressed as absorption in the matrix resin without glass or fillers).

One embodiment of the present invention is directed to a curable resin composition for composites and electrical laminates comprising (I) at least one thermoset resin composition; (II) at least one curing agent or hardener; and (III) at least one reinforcing material; wherein the composite or electrical laminate has a balance of properties including a combination of (a) a Tg of at least about 150° C.; and (b) a water uptake of less than about 2.5 wt %.

Another embodiment of the present invention is directed to laminates and composites prepared from an epoxy resin composition represented by the following general chemical structure of Formula I, such as for example, epoxy resins prepared from a dihydroxydiphenyl-cycloalkane compound:

Formula I

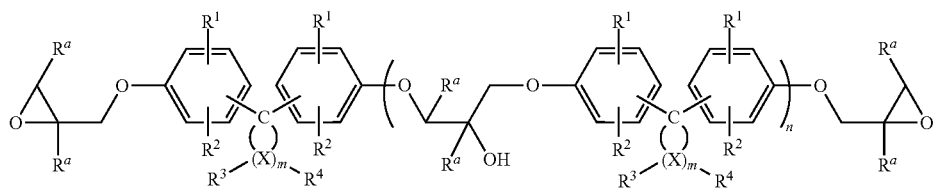

wherein $R^a$ is a hydrogen or methyl group; $R^1$ and $R^2$, independently from each other, each represents a hydrogen atom, a halogen, a substituted or unsubstituted alkyl group, a substituted or unsubstituted aryl group, or a substituted or unsubstituted aralkyl group; a nitrile group; a nitro group; a substituted or unsubstituted alkoxy group; X is $CH_2$, $CH(R^3)$, or $C(R^3)(R^4)$; m is an integral number between 8 and 20; $R^3$ and $R^4$, independently from each other, each represents a hydrogen atom, a halogen, a substituted or unsubstituted alkyl group, a substituted or unsubstituted aryl group, or a substituted or unsubstituted aralkyl group; and n is an integer having a value from 0 to about 10.

An example of a dihydroxydiphenyl-cycloalkane compound can be represented by the following general Formula IV:

Formula IV

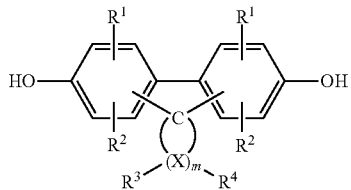

wherein $R^1$ and $R^2$, independently from each other, each represents a hydrogen atom, a halogen, a substituted or unsubstituted alkyl group, a substituted or unsubstituted aryl group, or a substituted or unsubstituted aralkyl group; X is $CH_2$, $CH(R^3)$, or $C(R^3)(R^4)$; m is an integral number between 8 and 20; and $R^3$ and $R^4$, independently from each other, each represents a hydrogen atom, a halogen, a substituted or unsubstituted alkyl group, a substituted or unsubstituted aryl group, or a substituted or unsubstituted aralkyl group.

Still another embodiment of the present invention is directed laminates and composites prepared from advanced resin compositions represented by the epoxy resin of Formula II or the phenolic resin of Formula III.

Formula II

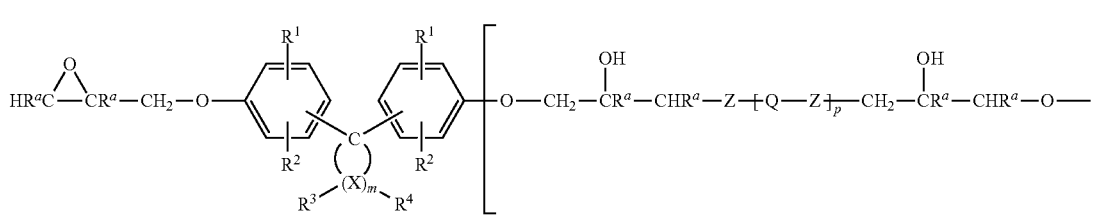

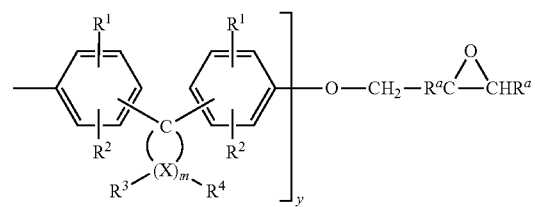

wherein $R^a$, $R^1$, $R^2$, $R^3$, $R^4$, X, and m are as defined in Formula I, y is an integer having a value from 1 to about 20; Q is a hydrocarbylene moiety, and each Z is independently selected from the group consisting of O, S, —$NR^b$, wherein $R^b$ is a hydrocarbyl moiety.

Formula III

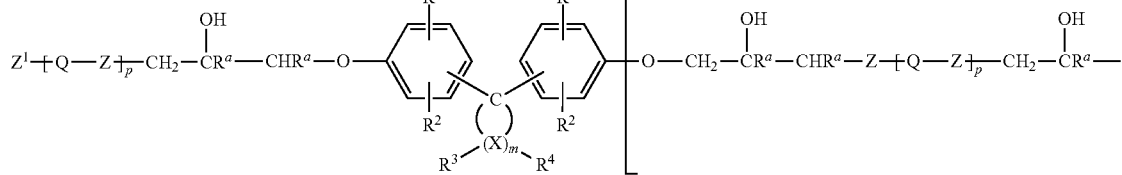

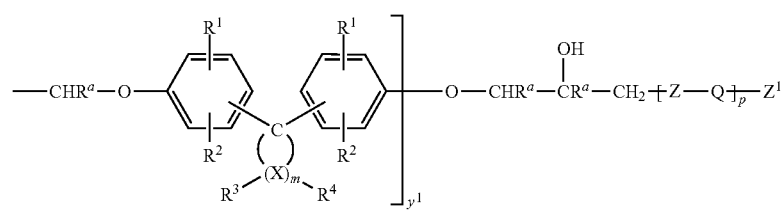

wherein $R^1$, $R^2$, $R^3$, $R^4$, $R^a$, X, and m are as defined in Formula I; p and $y^1$ are integers from 1 to about 20; Q is a hydrocarbylene moiety; each Z is independently selected from the group consisting of O, S, —$NR^b$, wherein $R^b$ is a hydrocarbyl moiety; and $Z^1$ is Z—H.

DETAILED DESCRIPTION OF THE INVENTION

According to the present invention, a curable resin composition (also referred to herein as a thermosettable composition or hardenable composition), useful for composites and electrical laminates of the present invention disclosed herein, may comprise (I) at least one thermoset resin composition; (II) at least one hardener; (III) at least one reinforcing material, wherein either the hardener or the resin (or both) are one of the compositions described by Formulas I, II, or III, and the composite or electrical laminate has a balance of desirable properties including a combination of: low water absorption and high glass transition temperature (Tg), and good dielectric properties.

The term "curable" means that the composition is capable of being subjected to conditions which will render the composition to a cured or thermoset state or condition.

The term "cured" or "thermoset" is defined by L. R. Whittington in Whittington's Dictionary of Plastics (1968) on page 239 as follows: "Resin or plastics compounds which in their final state as finished articles are substantially infusible and insoluble. Thermosetting resins are often liquid at some stage in their manufacture or processing, which are cured by heat, catalysis, or some other chemical means. After being fully cured, thermosets cannot be resoftened by heat. Some plastics which are normally thermoplastic can be made thermosetting by means of crosslinking with other materials."

Although the present invention is related to reinforced compositions, meaningful measurements of thermoset properties of the composition can be made without the reinforcement present. With these data the properties of the composites and laminates can be calculated by a weighted average of the properties of the thermoset and the reinforcement material. For example, water absorption is measured by first preparing a clear casting with no reinforcement. The freshly prepared casting is weighed and placed in a steam autoclave at 124° C. for 2 hours. The weight gain is then calculated as a percentage of the original weight. Thermosets of the present invention exhibit water absorptions of less than 2% in this test.

The Tg is measured using Differential Scanning calorimetry (DSC). This is an important property of all thermosets. Above this temperature the modulus drops precipitously, and every property changes significantly. For laminate and composite applications, high Tg's (>130° C.) are usually desirable. The Tg is highly dependant on the details of the formulation (especially the choice of the hardener when epoxies of Formula I or II are used, or the choice of epoxy when Formula III is used).

As non-limiting embodiments of the present invention, the thermoset resin composition, component (I), of the thermosettable composition of the present invention may be selected, for example, from the following:

(1) An epoxy resin represented by Formula I which is prepared from a dihydroxydiphenyl-cycloalkane compound:

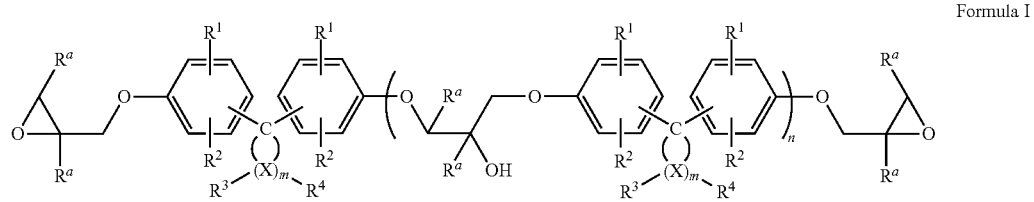

Formula I wherein $R^a$ is a hydrogen or methyl group; $R^1$ and $R^2$, independently from each other, each represents a hydrogen atom, a halogen, a substituted or unsubstituted alkyl group, a substituted or unsubstituted aryl group, or a substituted or unsubstituted aralkyl group; a nitrile group; a nitro group; a substituted or unsubstituted alkoxy group; X is $CH_2$, $CH(R^3)$, or $C(R^3)(R^4)$; m is an integral number between 8 and 20; $R^a$ is a hydrogen or methyl group; $R^3$ and $R^4$, independently from each other, each represents a hydrogen atom, a halogen, a substituted or unsubstituted alkyl group, a substituted or unsubstituted aryl group, or a substituted or unsubstituted aralkyl group; and n is an integer having a value from 0 to about 10.

In the Formula I above, the substituted or unsubstituted alkyl group, a substituted or unsubstituted aryl group, or a substituted or unsubstituted aralkyl group for $R^1$-$R^4$ and the substituted or unsubstituted alkoxy group for $R^1$ and $R^2$ may include, for example, a $C_1$-$C_8$ alkyl or alkyloxy group, a $C_6$-$C_{10}$ aryl group, or a $C_7$-$C_{12}$ aralkyl group.

As typically prepared the epoxy resins of Formula I are a mixture of oligomers with varying n, although the shortest member with n=0 predominates. For composite applications that involve fabrication without solvent, the presence of oligomers (n>0) is undesirable because they increase the viscosity of the formulation. In these cases the concentration of oligomers is preferably less than 50 wt %, more preferably less than 30 wt %, and most preferably less than 20 wt %.

(2) An advanced epoxy resin composition represented in Formula II, such those which are prepared by reacting one or more bisphenols with a stoichiometric excess of one or more of the epoxy resins of Formula I:

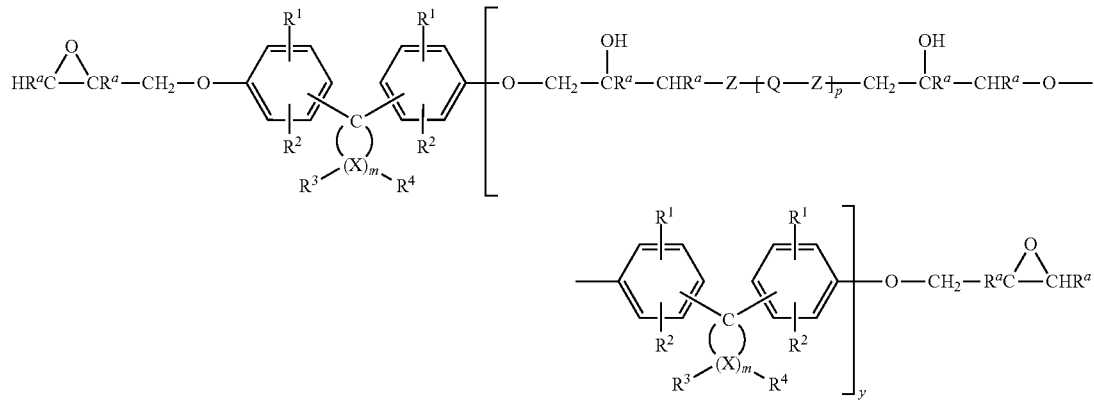

Formula II wherein $R^a$, $R^1$, $R^2$, $R^3$, $R^4$, X, and m are as defined in Formula I, y is an integer having a value from 1 to about 20; Q is a hydrocarbylene moiety, and each Z is independently selected from the group consisting of O, S, —$NR^b$, wherein $R^b$ is a hydrocarbyl moiety.

By "hydrocarbylene moiety" as used herein it is meant any divalent radical formed by removing two hydrogen atoms from a hydrocarbon. More specifically the hydrocarbylene moiety is a divalent moiety selected from the group consisting of an unsubstituted or substituted alkyl, an unsubstituted or substituted cycloalkyl, an unsubstituted or substituted polycycloalkyl, an unsubstituted or substituted alkenyl, an unsubstituted or substituted cycloalkenyl, an unsubstituted or substituted di or polycycloalkenyl, or an unsubstituted or substituted aromatic ring. By "hydrocarbyl moiety" used herein it is meant a monovalent radical, more specifically, any monovalent moiety selected from the group consisting of an unsubstituted or substituted alkyl, an unsubstituted or substituted cycloalkyl, an unsubstituted or substituted polycycloalkyl, an unsubstituted or substituted alkenyl, an unsubstituted or substituted cycloalkenyl, an unsubstituted or substituted di or polycycloalkenyl, or an unsubstituted or substituted aromatic ring.

The epoxy resin of Formula II is an advanced epoxy resin product prepared from (a) one or more epoxy resins of a dihydroxydiphenyl-cycloalkane compound given in Formula I with (b) one or more suitable compounds having an average of more than one reactive hydrogen atom per molecule, wherein the reactive hydrogen atom is reactive with an epoxide group in said epoxy resin. The epoxy resin used in the advancement reaction may additionally include (c) any one or more of the known epoxy resins, such as, for example, the diglycidyl ethers of dihydroxyaromatic compounds. The preparation of the aforementioned advanced epoxy resin products can be performed using known methods.

Examples of the compound having an average of more than one reactive hydrogen atom per molecule include dihydroxyaromatic, dithiol, disulfonamide, diamide or dicarboxylic acid compounds or compounds containing one primary amine or amide group, two secondary amine groups, one secondary amine group and one phenolic hydroxy group, one secondary amine group and one carboxylic acid group, or one phenolic hydroxy group and one carboxylic acid group, and any combination thereof.

The ratio of the compound having an average of more than one reactive hydrogen atom per molecule to the epoxy resin is generally from about 0.01:1 to about 0.95:1, preferably from about 0.05:1 to about 0.8:1, and more preferably from about 0.10:1 to about 0.5:1 equivalents of the reactive hydrogen atom per equivalent of the epoxide group in the epoxy resin.

The advancement reaction may be conducted in the presence or absence of a solvent with the application of heat and mixing. The advancement reaction may be conducted at atmospheric, superatmospheric or subatmospheric pressures and at temperatures of from about 20° C. to about 260° C., preferably, from about 80° C. to about 240° C., and more preferably from about 100° C. to about 200° C.

The time required to complete the advancement reaction depends upon factors such as the temperature employed, the chemical structure of the compound having more than one reactive hydrogen atom per molecule employed, and the chemical structure of the epoxy resin employed. Higher temperature may require shorter reaction time whereas lower temperature may require a longer period of the reaction time.

In general, the time for the advancement reaction completion may range from about 5 minutes to about 24 hours, preferably from about 30 minutes to about 8 hours, and more preferably from about 30 minutes to about 4 hours.

A catalyst may also be added in the advancement reaction. Examples of the catalyst may include phosphines, quaternary ammonium compounds, phosphonium compounds and tertiary amines. The catalyst may be employed in quantities from about 0.01 to about 3, preferably from about 0.03 to about 1.5, and more preferably from about 0.05 to about 1.5 percent by weight based upon the total weight of the epoxy resin.

Other details concerning an advancement reaction useful in preparing the advanced epoxy resin product for the resin compound which may be employed in the present invention are given in U.S. Pat. No. 5,736,620 and *Handbook of Epoxy Resins* by Henry Lee and Kris Neville, incorporated herein by reference.

Examples of the aromatic di and polyhydroxyl containing compound include the dihydroxydiphenyl-cycloalkanes derived from the reaction with of cyclooctanone, cyclodecanone, cyclododecanone, cyclopentadecanone, cyclooctadecanone, cycloeicosanone, and mixtures thereof with phenol; tetrabromobisphenol A; hydroquinone; resorcinol; catechol; 2,4-dimethylresorcinol; 4-chlororesorcinol; tetramethylhydroquinone; bisphenol A (4,4'-isopropylidenediphenol); 4,4'-dihydroxydiphenylmethane; 4,4'-thiodiphenol; 4,4'-sulfonyldiphenol; 2,2'-sulfonyldiphenol; 4,4'-dihydroxydiphenyl oxide; 4,4'-dihydroxybenzophenone; 1,1-bis(4-hydroxyphenyl)-1-phenylethane; 4,4'-bis(4(4-hydroxyphenoxy)-phenylsulfone)diphenyl ether; 4,4'-dihydroxydiphenyl disulfide; 3,3',3,5'-tetrachloro-4,4'-isopropylidenediphenol; 3,3',3,5'-tetrabromo-4,4'- isopropylidenediphenol; 3,3'-dimethoxy-4,4'-isopropylidenediphenol; 4,4'-dihydroxybiphenyl; 4,4'-dihydroxy-alpha-methylstilbene; 4,4'-dihydroxybenzanilide; bis(4-hydroxyphenyl)terephthalate; N,N'-bis(4-hydroxyphenyl)terephthalamide; bis(4'-hydroxybiphenyl)terephthalate; 4,4'-dihydroxyphenylbenzoate; bis(4'-hydroxyphenyl)-1,4-benzenediimine; 1,1'-bis(4-hydroxyphenyl)cyclohexane; phloroglucinol; pyrogallol; 2,2',5,5'-tetrahydroxydiphenylsulfone; tris(hydroxyphenyl)methane; dicyclopentadiene diphenol; tricyclopentadienediphenol; and any combination thereof.

Examples of the di- and polycarboxylic acids include 4,4'-dicarboxydiphenylmethane, terephthalic acid, isophthalic acid, 1,4-cyclohexanedicarboxylic acid, 1,6-hexanedicarboxylic acid, 1,4-butanedicarboxylic acid, dicyclopentadienedicarboxylic acid, tris(carboxyphenyl)methane, 1,1-bis(4-carboxyphenyl)cyclohexane, 3,3',5,5'-tetramethyl-4,4'-dicarboxydiphenyl, 4,4'-dicarboxy-alpha-methylstilbene, 1,4-bis(4-carboxyphenyl)-trans-cyclohexane, 1,1'-bis(4-carboxyphenyl)cyclohexane, 1,3-dicarboxy-4-methylbenzene, 1,3-dicarboxy-4-methoxybenzene, 1,3-dicarboxy-4-bromobenzene, 4,4'-benzanilidedicarboxylic acid; 4,4'-phenylbenzoatedicarboxylic acid; 4,4'-stilbenedicarboxylic acid and any combination thereof.

Examples of the di- and polymercaptans include 1,3-benzenedithiol, 1,4-benzenedithiol, 4,4'-dimercaptodiphenylmethane, 4,4'-dimercaptodiphenyl oxide, 4,4'-dimercapto-alpha-methylstilbene, 3,3',5,5'-tetramethyl-4,4'-dimercaptodiphenyl, 1,4-cyclohexanedithiol, 1,6-hexanedithiol, 2,2'-dimercaptodiethylether, 1,2-dimercaptopropane, bis(2-mercaptoethyl)sulfide, tris(mercaptophenyl)methane, 1,1-bis(4-mercaptophenyl)cyclohexane, and any combination thereof.

Examples of the di- and polyamines include 1,2-diaminobenzene, 1,3-diaminobenzene, 1,4-diaminobenzene, 4,4'-diaminodiphenylmethane, 4,4'-diaminodiphenylsulfone, 2,2'-diaminodiphenylsulfone, 4,4'-diaminodiphenyl oxide, 3,3',5,5'-tetramethyl-4,4'-diaminodiphenyl, 3,3'-dimethyl-4,4'-diaminodiphenyl, 4,4'-diamino-alpha-methylstilbene, 4,4'-diaminobenzanilide, 4,4'-diaminostilbene, 1,4-bis(4-aminophenyl)-trans-cyclohexane, 1,1-bis(4-aminophenyl)cyclohexane, tris(aminophenyl)methane, 1,4-cyclohexanediamine, 1,6-hexanediamine, piperazine, ethylenediamine, diethyletriamine, triethylenetetramine, tetraethylenepentamine, 1-(2-aminoethyl)piperazine, bis(aminopropyl)ether, bis(aminopropyl)sulfide, bis(aminomethyl)norbornane, 2,2'-bis(4-aminocyclohexyl)propane, and any combination thereof.

Examples of the primary monoamines include aniline, 4-chloroaniline, 4-methylaniline, 4-methoxyaniline, 4-cyanoaniline, 2,6-dimethylaniline, 4-aminodiphenyl oxide, 4-aminodiphenylmethane, 4-aminodiphenylsulfide, 4-aminobenzophenone, 4-aminodiphenyl, 4-aminostilbene, 4-amino-alpha-methylstilbene, methylamine, 4-amino-4'-nitrostilbene, n-hexylamine, cyclohexylamine, aminonorbornane, and any combination thereof.

Examples of the sulfonamides include phenylsulfonamide, 4-methoxyphenylsulfonamide, 4-chlorophenylsulfonamide, 4-bromophenylsulfonamide, 4-methylsulfonamide, 4-cyanosulfonamide, 2,6-dimethyphenylsulfonamide, 4-sulfonamidodiphenyl oxide, 4-sulfonamidodiphenylmethane, 4-sulfonamidobenzophenone, 4-sulfonylamidodiphenyl, 4-sulfonamidostilbene, 4-sulfonamido-alpha-methylstilbene, and any combination thereof.

Examples of the aminophenols include o-aminophenol, m-aminophenol, p-aminophenol, 2-methoxy-4-hydroxyaniline, 3,5-dimethyl-4-hydroxyaniline, 3-cyclohexyl-4-hydroxyaniline, 2,6-dibromo-4-hydroxyaniline, 5-butyl-4-hydroxyaniline, 3-phenyl-4-hydroxyaniline, 4-(1-(3-aminophenyl)-1-methylethyl)phenol, 4-(1-(4-aminophenyl)ethyl)phenol, 4-(4-aminophenoxy)phenol, 4-((4-aminophenyl)thio)phenol, (4-aminophenyl)(4-hydroxyphenyl)methanone, 4-((4-aminophenyl)sulfonyl)phenol, 4-(1-(4-amino-3,5-dibromophenyl)-1-methylethyl)-2,6-dibromophenol, N-methyl-p-aminophenol, 4-amino-4'-hydroxy-alpha-methylstilbene, 4-hydroxy-4'-amino-alpha-methylstilbene, and any combination thereof.

Examples of the aminocarboxylic acids include 2-aminobenzoic acid, 3-aminobenzoic acid, 4-aminobenzoic acid, 2-methoxy-4-aminobenzoic acid, 3,5-dimethyl-4-aminobenzoic acid, 3-cyclohexyl-4-aminobenzoic acid, 2,6-dibromo-4-aminobenzoic acid, 5-butyl-4-aminobenzoic acid, 3-phenyl-4-aminobenzoic acid, 4-(1-(3-aminophenyl)-1-methylethyl)benzoic acid, 4-(1-(4-aminophenyl)ethyl)benzoic acid, 4-(4-aminophenoxy)benzoic acid, 4-((4-aminophenyl)thio)benzoic acid, (4-aminophenyl)(4-carboxyphenyl)methanone, 4-((4-aminophenyl)sulfonyl)benzoic acid, 4-(1-(4-amino-3,5-dibromophenyl)-1-methylethyl)-2,6-dibromobenzoic acid, N-methyl-4-aminobenzoic acid, 4-amino-4'-carboxy-alpha-methylstilbene, 4-carboxy-4'-amino-alpha-methylstilbene, glycine, N-methylglycine, 4-aminocyclohexanecarboxylic acid, 4-aminohexanoic acid, 4-piperidinecarboxylic acid, 5-aminophthalic acid, and any combination thereof.

Examples of the sulfanilamides include o-sulfanilamide, m-sulfanilamide, p-sulfanilamide, 2-methoxy-4-aminobenzoic acid, 2,6-dimethyl-4-sulfonamido-1-aminobenzene, 3-methyl-4-sulfonamido-1-aminobenzene, 5-methyl-3-sulfonamido-1-aminobenzene, 3-phenyl-4-sulfonamido-1-aminobenzene, 4-(1-(3-sulfonamidophenyl)-1-methylethyl)aniline, 4-(1-(4-sulfonamidophenyl)ethyl)aniline, 4-(4-sulfonamidophenoxy)aniline, 4-((4-sulfonamidophenyl)thio)aniline, (4-sulfonamidophenyl)(4-aminophenyl)methanone, 4-((4-sulfonamidophenyl)sulfonyl)aniline, 4-(1-(4-sulfonamido-3,5-dibromophenyl)-1-methylethyl)-2,6-dibromoaniline, 4-sulfonamido-1-N-methylaminobenzene, 4-amino-4'-sulfonamido-alpha-methylstilbene, 4-sulfonamido-4'-amino-alpha-methylstilbene, and any combination thereof.

(3) An advanced active hydrogen-containing composition represented in Formula III, which is prepared by reacting one or more bisphenols with a stoichiometric deficiency of one or more of the epoxy resins of Formula I:

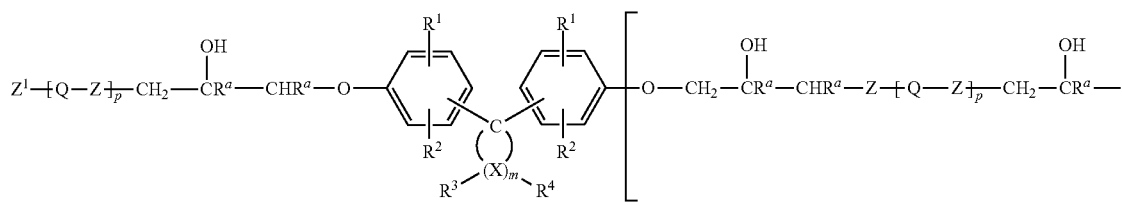

Formula III

-continued

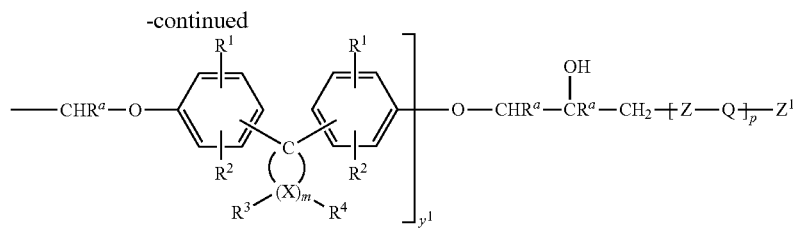

wherein $R^a$, $R^1$, $R^2$, $R^3$, $R^4$, X, p and m are as defined in Formula I, $y^1$ is an integer having a value from 0 to about 20; Q is a hydrocarbylene moiety, each Z is independently selected from the group consisting of O, S, —$NR^b$, wherein $R^b$ is a hydrocarbyl moiety; and $Z^1$ is Z—H.

The terms "hydrocarbylene moiety" and "hydrocarbyl moiety" are used as hereinbefore defined.

Any one of the thermoset resin compositions described above which can serve as component (I) of the thermosettable composition of the present invention, can include any of the thermoset resin compositions described in U.S. Provisional Patent Application Ser. No. 61/265,799, filed on even date herewith by Metral et al., incorporated herein by reference, and published on Sep. 20, 2012 as U.S. Publication 2012/0238709. The method of manufacturing component (I) is also described in the above U.S. Provisional Patent Application Ser. No. 61/265,799.

Component (I) may be cured in accordance with well known techniques used by those skilled in the art of curing conventional thermoset resins such as epoxy resins, including for example, mixing a curing agent, component (II) with component (I) in the appropriate ratio; and subjecting the thermosettable composition comprising the mixture of components (I) and (II) to curing conditions.

The curing agent, component (II), (also referred to as a hardener or cross-linking agent) useful in the thermosettable composition, may be selected, for example, from those curing agents well known in the art including, but are not limited to, anhydrides, carboxylic acids, amine compounds, phenolic compounds, polyols, or mixtures thereof. The term "curing agent" as used herein is intended to also include catalysts or co-catalysts used either alone or in conjunction with one or more other curing agents.

Examples of the curing agent useful in the present invention include any of the curing materials known to be useful for curing epoxy resin based compositions. Such materials include, for example, polyamine, polyamide, polyaminoamide, polyphenol, polymeric thiol, polycarboxylic acid and anhydride, polyol, and any combination thereof or the like. Other specific examples of the curing agent include dicyandiamide, phenol novolacs, bisphenol-A novolacs, phenol novolac of dicyclopentadiene, styrene-maleic acid anhydride (SMA) copolymers; and any combination thereof. Preferred examples of the hardener may include phenol novolac, cresol novolac, bisphenol A, dicyandiamide, and any combination thereof.

Dicyandiamide may be one preferred embodiment of the curing agent useful in the present invention. Dicyandiamide has the advantage of providing delayed curing since dicyandiamide requires relatively high temperatures for activating its curing properties; and thus, dicyandiamide can be added to a thermosetting resin and stored at room temperature (about 25° C.). Additionally, the curing profile of a resin composition using dicyandiamide may be conveniently modified using a catalyst, such as, for example, 2-methylimidazole (2-MI).

In general, the concentration of the curing agent, component (II), present in the thermosettable resin composition of the present invention may vary depending on the end use application. For example, the amount of curing agent used may vary from about 0.1 to about 150 parts per hundred parts thermosettable resin, by weight, in some embodiments. In other embodiments, the curing agent may be used in an amount ranging from about 5 to about 95 parts per hundred parts thermosettable resin, by weight; and the curing agent may be used in an amount ranging from about 10 to about 90 parts per hundred parts theremosettable resin, by weight, in yet other embodiments.

In another embodiment of the present invention, component (I) may be cured in accordance with well known techniques used by those skilled in the art of curing conventional epoxy resins, including for example, mixing component (I) as described above with component (III) at least one thermosetting resin other than the compound of component (I) in the appropriate ratio; and subjecting the thermosettable composition comprising the mixture of components (I) and (II) to curing conditions. In this embodiment, the curing agent may be optional, particularly in the instance wherein the component (I) contains reactive functionalities that can react with the thermosetting resin without the use of a curing agent. The optional curing agent may be any of the curing agents described above.

The other thermosetting resin useful as component (III), may include, for example, at least one thermoset resin component selected from epoxy resins, isocyanate resins, (meth)acrylic resins, phenolic resins, vinylic resins, styrenic resins, polyester resins, vinylester resins, silicone resins, melamine resins; and mixtures thereof. Preferably, an epoxy resin is employed as component (III) which is different from component (I) in the thermosettable resin composition.

Examples of the other thermoset resin different from component (I), suitable for use in the present invention may include epoxidized bisphenol A; epoxidized dihydroxydiphenyl-cycloalkane such as epoxidized bisphenol cyclododecanone; epoxidized phenolic novolac (multifunctional) such as epoxidized phenol novolac, bisphenol A novolac, or epoxidized bisphenol dicyclopentadiene novolac; epoxidized bromine-containing bisphenol or brominated bisphenol A novolac; epoxidized phosphorus-containing bisphenol A; or any combination thereof, where "epoxidized" represents treatment with epichlorohydrin (or related material) to convert each phenolic-OH to the glycidyl ether.

The other thermosetting resin, component (III), may be present in the thermosettable composition at a concentration less than about 80 mol % of the epoxy in the formulation, preferably less than about 50 mol %, and more preferably less than 30 mol %.

In one preferred embodiment, the other thermosetting resin useful as component (III), in the present invention includes at least one epoxy resin. The term "epoxy resin" herein means a compound which possesses one or more vicinal epoxy groups per molecule, i.e., at least one 1,2-epoxy group per molecule.

In general, the epoxy resin compound may be a saturated or unsaturated aliphatic, cycloaliphatic, aromatic or heterocyclic compound which possesses at least one 1,2-epoxy group. Such compounds can be substituted, if desired, with one or more inert substituents, such as halogen atoms, aliphatic or cycloaliphatic hydroxy groups, ether radicals, lower alkyls and the like. By "inert" with reference to substituents, it is meant that the substituents are substantially non-reactive with the epoxide groups and other functional groups. The epoxy resin compound may also be monomeric, oligomeric or polymeric, i.e., the epoxy resin may be selected from a monoepoxide, a diepoxide, a multi-functional epoxy resin, a polyepoxide; an advanced epoxy resin; or mixtures thereof. An extensive enumeration of epoxy resins useful in the present invention is found in Lee, H. and Neville, K., "Handbook of Epoxy Resins," McGraw-Hill Book Company, New York, 1967, Chapter 2, pages 257-307; incorporated herein by reference.

The epoxy resins useful in the present invention may vary and include conventional and commercially available epoxy resins, which may be used alone or in combinations of two or more. In choosing epoxy resins for compositions disclosed herein, consideration should not only be given to properties of the final product, but also to viscosity and other properties that may influence the processing of the resin composition.

Particularly suitable epoxy resins known to the skilled worker are based on reaction products of polyfunctional alcohols, phenols, cycloaliphatic carboxylic acids, aromatic amines, or aminophenols with epichlorohydrin. A few non-limiting embodiments include, for example, bisphenol A diglycidyl ether, bisphenol F diglycidyl ether, resorcinol diglycidyl ether, and the triglycidyl ether of para-aminophenol. Other suitable epoxy resins known to the skilled worker include reaction products of epichlorohydrin with o-cresol and, respectively, phenol novolacs. It is also possible to use a mixture of two or more of any of the above epoxy resins.

The epoxy resins useful in the present invention for the preparation of the thermoset composition, component (III), may be selected from commercially available products. For example, D.E.R.™ 331, D.E.R.™ 332, D.E.R.™ 334, D.E.R.™ 580, D.E.N.™ 431, D.E.N.™ 438, D.E.R.™ 736, or D.E.R.™ 732 available from The Dow Chemical Company may be used. As an illustration of the present invention, the epoxy resin component of the present invention may be a liquid epoxy resin, D.E.R.™ 383 (DGEBPA) having an epoxide equivalent weight of 175-185, a viscosity of 9.5 Pa-s and a density of 1.16 gm./cc. Other commercial epoxy resins that can be used for the epoxy resin component can be D.E.R.™ 330, D.E.R.™ 354, or D.E.R.™ 332.

Other suitable epoxy resins useful in the present invention are disclosed in, for example, U.S. Pat. Nos. 3,018,262; 7,163,973, 6,887,574; 6,632,893; 6,242,083; 7,037,958; 6,572,971; 6,153,719; 5,405,688; PCT Publication WO 2006/052727; U.S. Patent Application Publication Nos. 20060293172 and 20050171237, each of which is incorporated herein by reference.

The EEW of the epoxy resins useful in the present invention is generally from about 100 grams per epoxy equivalent (g/eq) to about 20,000 g/eq and more preferably from about 500 g/eq to about 5000 g/eq. As used herein the term EEW refers to the average molecular weight of the epoxide moiety in grams per equivalent (g/eq) divided by the average number of epoxide groups present in the molecule. Examples of diepoxides useful in the present invention are the epoxy resins having an EEW of from about 100 g/eq to about 4000 g/eq.

In general, the viscosity of the epoxy compound used in the present invention is from 0 mPas to about 10000 mPas, preferably from about 1 mPas to about 1000 mPas, and most preferably from about 5 mPas to about 500 mPas.

Other epoxy resins useful as at least one thermoset resin of component (III) include an epoxidized dihydroxydiphenyl cycloalkane, an epoxidized phenol novolac, a bromine-containing epoxy resin, a phosphorus-containing resin, and combinations thereof.

More specific embodiments of the epoxy resins useful in the present invention may include for example an epoxidized bisphenol cyclododecanone, an epoxidized bisphenol A novolac, an epoxidized bisphenol dicyclopentadiene novolac, an epoxidized bromine-containing bisphenol A novolac, or any combination thereof.

In general, in one embodiment, component (III) may be present in the curable composition in an amount of less than about 80 wt %; preferably, less than about 60 wt %; and more preferably, less than about 50 wt % based on the total weight of the composition.

Fillers can be used in the formulation for a variety of purposes, such as modifying the rheology, reducing cost, reducing the coefficient of thermal expansion, and improving the flame retardancy. Examples of some preferred fillers may include silica, talc, alumina, quartz, mica, flame retardants, metallic powders, and any combination thereof. Examples of flame retardant fillers may include aluminum trihydroxide, magnesium hydroxide, phosphinites such as aluminum or zinc phosphinites, or boehmite.

In general, for applications where a filler is desirable, it may be present in the thermoset resin is from about 0.1 percent to about 95 percent by weight, preferably, from about 10 percent to about 90 percent by weight, more preferably, from about 10 percent to about 85 percent by weight, even more preferably, from about 20 percent to about 80 percent by weight, and most preferably, from about 20 percent to about 75 percent by weight based on the total weight of the thermoset resin.

The filler is generally in a particle form and has an average particle dimension below about 1 mm, preferably below about 100 micron, more preferably below about 50 micron, and most preferably below about 10 micron, and above about 2 nm, preferably above about 10 nm, more preferably above about 20 nm, and most preferably above about 50 nm.

The reinforcing or reinforcement material useful for composite or electrical laminate resin formulation of the present invention may include any of the fibrous reinforcement materials known in the art including for example natural and synthetic fibers in the form of woven fabric, mat, monofilament, multifilament, unidirectional fiber, roving, random fiber or filament, inorganic filler or whisker, or hollow sphere. Other suitable reinforcing material may include fibers such as carbon (graphite), boron, glass, ceramics, nylon, rayon, cotton, aramid, graphite, polyalkylene terephthalates, polyethylene, polypropylene, polyesters, and any combination thereof.

An aspect shaped inorganic material which has similar properties suitable for a reinforcement material may also be used. The aspect shaped inorganic material may include inorganic clays such as montmorillonites, fluoromicas, boehmites, and the like.

Other examples of the fibrous reinforcement materials useful for the curable electrical laminate or composite composition of the present invention may include those classified by the international glass style: 1020, 104, 106, 1065, and 7628.

Other fibrous reinforcing material may be a fiber, including for example, carbon/graphite; boron; quartz; aluminum oxide; glasses of various moduli such as 'E' and 'S'; and silicon carbide or silicon carbide fibers containing titanium.

Commercially available fibers may include organic fibers, such as KEVLAR® (trademark of Dupont); aluminum oxide-containing fibers, such as NEXTEL® (trademark of 3M); silicon carbide fibers, such as NICALON® (trademark of Nippon Carbon); and silicon carbide fibers containing titanium, such as TYRRANO® (trademark of Ube).

The amount of reinforcing material in the composite or electrical laminate composition may vary depending on the type and form of the reinforcing material and the expected end product. In general, the thermoset composite of the present invention may comprise a fibrous reinforcement material or an aspect shaped inorganic material, in an amount of from about 1 wt % to about 90 wt %; preferably, from about 10 wt % to about 80 wt %; and more preferably, from about 20 wt % to about 70 wt % based on the total weight of the composition.

When the reinforcing material or fibrous reinforcement material component is a fiber, it may be present in the thermosettable resin composition of the present invention in an amount of from about 10 wt % to about 90 wt %; preferably, from about 20 wt % to about 80 wt %; and more preferably, from about 30 wt % to about 70 wt % based on the total weight of the composition.

The fibers may be sized or unsized. When the fibers are sized, the sizing on the fibers is typically a layer 100 to 200 nm thick. When glass fibers are used, the sizing may be, for example, a coupling agent, lubricant, anti-static agent, or a combination thereof.

The fiber reinforcement may have various forms, and may be continuous or discontinuous, or combinations thereof. Continuous strand roving may be used to fabricate unidirectional or angle-ply composites. Continuous strand roving may also be woven into fabric or cloth using different weaves such as plain, satin, leno, crowfoot, and 3-dimensional. Other forms of continuous fiber reinforcement are exemplified by braids, stitched fabrics, and unidirectional tapes and fabrics.

Discontinuous fibers suitable for this invention may include milled fibers, whiskers, chopped fibers, and chopped fiber mats. When the reinforcing material is discontinuous, it may be present in the thermosettable resin composition of the present invention in an amount of from about 10 wt % to about 90 wt %; preferably, from about 20 wt % to about 80 wt %; and more preferably, from about 30 wt % to about 70 wt % based on the total weight of the composition.

Examples of suitable discontinuous reinforcing materials include milled or chopped fibers, such as glass and calcium silicate fibers. An example of a discontinuous reinforcing material is a milled fiber of calcium silicate (wollastonite; NYAD G SPECIAL®, trademark of Nyco.

A combination of continuous and discontinuous fibers may be used in the same composite. For example, a woven roving mat is a combination of a woven roving and a chopped strand mat, and it is suitable for use in embodiments disclosed herein.

A hybrid comprising different types of fibers may also be used. For example, layers of different types of reinforcement may be used. In aircraft interiors, for example, the reinforcing material may include a fiber and a core, such as a NOMEX® (trademark of DuPont) honeycomb core, or a foam core made of polyurethane or polyvinylchloride.

The thermosettable electrical laminate composite composition of the present invention may further comprise one or more optional added components such as for example, a catalyst, a flame retardant or a solvent.

An optional component useful in the thermosettable composition of the present invention includes at least one catalyst. The catalyst used in the present invention may be adapted for polymerization, including homopolymerization, of the at least one thermosetting resin. Alternatively, catalyst used in the present invention may be adapted for a reaction between the at least one thermosetting resin and the at least one curing agent.

The catalyst useful as an optional component in the thermosettable composition of the present invention may be any catalyst well known in the art used for this purpose. For example, the catalyst may include compounds containing amine, phosphine, heterocyclic nitrogen, ammonium, phosphonium, sulfonium moieties, substituted derivative thereof, and any combination thereof. Some non-limiting examples of the catalyst useful in the present invention may include, for example, ethyltriphenylphosphonium; benzyltrimethylammonium chloride; heterocyclic nitrogen-containing catalysts described in U.S. Pat. No. 4,925,901, incorporated herein by reference; imidazoles; triethylamine; and any combination thereof.

The selection of the catalyst useful in the present invention is not limited and commonly used catalysts for epoxy systems can be used. Also, the addition of a catalyst is optional and depends on the system prepared. When the catalyst is used, preferred examples of catalyst include tertiary amines, imidazoles, organophosphines, and acid salts.

Most preferred catalysts include tertiary amines such as, for example, triethylamine, tripropylamine, tributylamine, 2-methylimidazole, benzyldimethylamine, mixtures thereof and the like. Especially preferred are the alkyl-substituted imidazoles; 2,5-chloro-4-ethyl imidazole; and phenyl-substituted imidazoles, and any mixture thereof.

Even more preferred embodiments of the catalyst suitable for the present invention include for example 2-methyl imidazole, 2-phenyl imidazole, imidazole derivative, 1,8-Diazabicyclo[5.4.0]undec-7-ene (DBU), 2-methyl imidazole-epoxy resin adduct, such as EPON™ P101 (available from Hexion Specialty Chemicals), and any combination thereof.

In general, the concentration of the catalyst present in the thermosettable resin composition of the present invention may vary depending on the end use application. The amount of catalyst used may vary from about 0.1 to about 20 parts per hundred parts thermosettable resin, by weight, in some embodiments. In other embodiments, catalyst may be used in an amount ranging from about 1 to about 15 parts per hundred parts thermosettable resin, by weight; and from about 2 to about 10 parts per hundred parts thermosettable resin, by weight, in yet other embodiments. The specific amount of catalyst used for a given system may be determined experimentally through simple range finding experiments to develop the optimum in properties desired.

An optional component useful in the thermosettable composition of the present invention includes at least one chain extender. Examples of the optional chain extender useful as an additive in the composition of the present invention may include a dihydroxydiphenyl-cycloalkane such as bisphenol cyclododecanone, bisphenol A; dicyandiamide; phenol novolac such as bisphenol A novolac or phenol dicyclopentadiene novolac; bromine-containing bisphenol A such as tetrabromobisphenol A (TBBA); bromine-containing bisphenol A novolac; phosphorus-containing bisphenol A novolac; or any combination thereof.

In general, the additional optional chain extender used in the composition may be present in an amount of less than about 50 wt %; preferably, less than 30 wt %; and more preferably, less than about 25 wt % based on the total weight of the composition.

Examples of the flame retardants suitable to be used in the present invention may include a flame retardant epoxy resin such as bromine containing epoxy resins or "bromine-free" epoxy resins such as a phosphorous-containing epoxy resin.

Examples of the bromine containing epoxy resins of the present invention may include tetrabromobisphenol A, diglycidyl ether of tetrabromobisphenol A, and other brominated epoxies such as those commercially available from The Dow Chemical Company under the trademarks D.E.R. 560, D.E.R 542, D.E.R 592, D.E.R 593, D.E.R 530 and D.E.R 538; and mixtures thereof. A preferred epoxy resin containing bromine used in the present invention includes diglycidyl ether of tetrabromobisphenol A such as D.E.R. 560.

Two or more different bromine-containing epoxy resins may be blended together to make up the flame retardant epoxy component of the present invention. The bromine content of the epoxy resin may be from about 5 percent to about 50 percent by weight, preferably from about 10 percent to about 25 percent by weight, and more preferably from about 18 percent to about 21 percent by weight based on the total weight of the bromine-containing epoxy resin.

Another example of a flame retardant epoxy resin useful in the present invention is a "bromine-free" epoxy resin such as a phosphorous-containing epoxy resin. Examples of phosphorous-containing epoxy resins include methyl diglycidyl phosphonate, ethyl diglycidyl phosphonate, propyl diglycidyl phosphonate, butyl diglycidyl phosphonate, vinyl diglycidyl phosphonate, phenyl diglycidyl phosphonate and biphenyl diglycidyl phosphonate; methyl diglycidyl phosphate, ethyl diglycidyl phosphate, n-propyl diglycidyl phosphate, n-butyl diglycidyl phosphate, isobutyl diglycidyl phosphate, allyl diglycidyl phosphate, phenyl diglycidyl phosphate, p-methoxyphenyl diglycidyl phosphate, p-ethoxyphenyl diglycidyl phosphate, p-propyloxyphenyl diglycidyl phosphate, p-isopropyloxyphenyl diglycidyl phosphate, phenylthiodiglycidyl phosphate, triglycidyl phosphate, tris(glycidylethyl) phosphate, p-glycidyl-phenyl ethyl glycidyl phosphate, benzyl diglycidyl thiophosphate, and combinations thereof.

More examples of phosphorous-containing epoxy resins may be selected from those described in U.S. Pat. No. 5,376,453, U.S. Application No. 2002/0119317A1, U.S. Pat. No. 6,403,220, and PCT Publication No. WO 99/00451, all of which are incorporated herein by reference.

Other examples of a phosphorous-containing epoxy resins useful in the present invention may include those obtained by epoxidizing a phosphorus element-containing compound including the epoxidized product of a phosphorus element-containing compound such as 9,10-dihydro-9-oxa-10-phosphaphenanthrene-10-oxide such as "Sanko-HCA," commercially available from Sanko of Japan, or "Struktol Polydis PD 3710," commercially available from Schill-Seilacher of Germany; 10(2',5'-dihydroxyphenyl)-9,10-dihydro-9-oxa-10-phosphaphenanthrene-10-oxide (such as "Sanko HCA-HQ"); bis(4-hydroxyphenyl)phosphine oxide; tris(2-hydroxyphenyl)phosphine oxide; dimethyl-1-bis(4-hydroxyphenyl) 1-phenylmethylphonate; tris(2-hydroxy-4/5-methylphenyl)phosphine oxide tris(4-hydroxyphenyl) phosphine oxide, bis(2-hydroxyphenyl)phenylphosphine oxide, bis(2-hydroxyphenyl)phenylphosphinate, tris(2-hydroxy-5-methylphenyl)phosphine oxide; or mixtures thereof. The epoxidizing of the phosphorus element-containing compound is general carried out with an epihalohydrin such as epichlorohydrin.

The thermosettable resin composition of the present invention may comprise at least one or more phosphorous-containing epoxy resins. Two or more different phosphorous-containing epoxy resins may be blended together to make up the flame retardant epoxy component in the thermosettable resin composition.

The phosphorous content of the epoxy resin composition may be from about 0.05 percent to about 20 percent by weight, preferably, from about 1 percent to about 10 percent by weight, and more preferably, from about 0.2 percent to about 5 percent by weight based on the total weight of the phosphorous-containing epoxy resin.

The bromine-containing epoxy resin and the phosphorous-containing epoxy resin may be used alone, or mixed together, or combined with other non-flame retardant epoxy resins. The non-flame retardant epoxy resin may be a halogenated, other than bromine, epoxy resin. The non-bromine halogenated epoxy resin may be, for example, a chlorine-containing epoxy resin. The non-flame retardant epoxy resin may also be a non-halogenated epoxy resin such as the diglycidyl ether of bisphenol A. When halogenated flame retardants are used, the halogen is present from about 5% to about 25 wt %, more preferably from 10 to 20 wt %, and most preferably from 14-20 wt %.

Examples of solvents useful for the thermosettable electrical laminate composite composition of the present invention may include glycol ethers such as those commercially available Dowanol™ P series from The Dow Chemical Company, ketones such as acetone or methyl ethyl ketone (MEK).

In general, the thermosettable electrical laminate composite composition of the present invention may comprise a solvent component in an amount of from about 5 wt % to about 80 wt %; preferably, from about 10 wt % to about 60 wt %; and more preferably, from about 20 wt % to about 50 wt % based on the total weight of the composition.

The thermosettable composition of the present invention may include optional additives and fillers conventionally found in thermosettable resin systems such as, for example, epoxy resin systems. The thermosettable compositions of the present invention may optionally contain additives and/or fillers which are useful for their intended uses. The type and amount of the additives and/or fillers used in the thermosettable resin composition will depend on the intended use of the thermosettable resin composition.

For example, the optional additives and fillers useful in the present invention composition may include, but not limited to, silica, glass, talc, metal powders, titanium dioxide, wetting agents, pigments, coloring agents, mold release agents, toughening agents, coupling agents, degassing agents, flame retardants (e.g., inorganic flame retardants, halogenated flame retardants, and non-halogenated flame retardants such as phosphorus-containing materials), ion scavengers, UV stabilizers, flexibilizing agents, tackifying agents, stabilizers, surfactants, flow modifiers, fillers, pigments or dyes, gloss control agents, antioxidants, matting agents curing initiators, curing inhibitors, thermoplastics, processing aids, UV blocking compounds, fluorescent compounds, UV stabilizers, inert fillers, fibrous reinforcements, antioxidants, impact modifiers including thermoplastic particles, and mixtures thereof. Additives and fillers may also include fumed silica, aggregates such as glass beads, polytetrafluoroethylene, polyol resins, polyester resins, phenolic resins, graphite, molybdenum disulfide, abrasive pigments, viscosity reducing agents, boron nitride, mica, nucleating agents, and stabilizers, among others. Fillers and modifiers may be preheated to drive off moisture prior to addition to the thermosettable resin composition. Additionally, these optional additives may have an effect on the properties of the composition, before and/or after curing, and should be taken into account when formulating the composition and the desired reaction product. The above list is intended to be exemplary and not limiting. The preferred additives for the, formulation of the present invention may be optimized by the skilled artisan.

Preferably, the additives used in the present invention include catalyst, co-catalysts, accelerators; and optionally other application-specific additives such as flame retardants, wetting agents, defoamers, adhesion promoters, fillers, pigments, dyes, stabilizers, UV-absorbers, and toughening agents. As is known in the art, it is possible to add other thermosetting monomers such as other epoxies, cyanates, maleimides, triazines, and benzoxazines, as well as other oligomers or polymers such as poly(phenylene oxide).

The concentration of the additional additives is generally between about 0 wt % to about 50 wt %, preferably between about 0.01 wt % to about 20 wt %, more preferably between about 0.05 wt % to about 15 wt %, and most preferably between about 0.1 wt % to about 10 wt % based on the weight of the total composition. Below about 0.01 wt %, the additives generally do not provide any further significant advantage to the resultant thermoset product; and above about 20 wt %, the properties improvement brought by these additives remains relatively constant.

Curable compositions may include from about 0.1 to about 50 volume percent optional additives in some embodiments. In other embodiments, curable compositions may include from about 0.1 to about 5 volume percent optional additives; and from about 0.5 to about 2.5 volume percent optional additives in yet other embodiments.

The curable compositions of the present invention disclosed herein includes (I) at least one thermoset resin composition; (II) at least one curing agent; and (III) at least one reinforcing material; wherein the composite or electrical laminate has the following properties a) a Tg of at least 150° C. and b) a water absorption of less than 0.5 wt %. In some embodiments, curable compositions disclosed herein may additionally include a filler, a flame retardant, a catalyst, a solvent, or other additives as described above.

Generally, curable compositions may be formed by admixing the above components in stages or simultaneously in the desired amounts to form the curable composition. The components of the formulation or composition of the present invention may be admixed to provide the curable composition of the present invention; and the final curable formulation of the present invention can be cured under conventional processing conditions to form a thermoset.

Fiber reinforced composites, for example, may be formed by hot melt prepregging. The prepregging method is characterized by impregnating bands or fabrics of continuous fiber with a thermosettable resin composition as described herein in molten form to yield a prepreg, which is laid up and cured to provide a composite of fiber and thermoset resin.

Other processing techniques can be used to form composites containing the thermosettable resin compositions disclosed herein. For example, filament winding, solvent prepregging, and pultrusion are typical processing techniques in which the uncured thermosettable resin may be used. Moreover, fibers in the form of bundles may be coated with the uncured thermosettable resin composition, laid up by filament winding, and cured to form a composite.

In some embodiments, composites may be formed by curing the curable thermosettable resin compositions disclosed herein. In other embodiments, composites may be formed by applying a thermosettable resin composition to a reinforcing material, such as by impregnating or coating the reinforcing material, and then curing the curable thermosettable resin composition.

Curing of the thermosettable resin compositions disclosed herein usually requires a temperature of at least about 30° C., up to about 250° C., for periods of minutes up to hours, depending on the thermosettable resin used, the curing agent used, and the catalyst, if used, if any. In other embodiments, curing may occur at a temperature of at least 100° C., for periods of minutes up to hours. Post-treatments may be used as well, such post-treatments ordinarily being at temperatures between about 100° C. and 200° C.

According to one embodiment of the present invention, thermosettable compositions, i.e., curable or hardenable compositions, of the present invention disclosed herein, may be useful for making electrical laminate, for example, for printed wiring boards (PWB). In one embodiment, of the electrical laminate composite composition comprises (I) at least one thermoset composition; and (II) at least one curing agent; (III) at least one thermoset resin different from component (I); (IV) at least one filler; and/or (V) at least one high strength fibrous reinforcement material.

One common problem of the PWB manufacturing using conventional thermoset resin material with high glass transition temperature (Tg) is that the high Tg thermoset resin material tends to have low toughness which causes brittle failures during the manufacturing, for example, a clean hole can not be produced within the PWB. The resulting thermoset resin products made from the thermosettable compositions of the present invention, however, have higher toughness and thus provide improved drillability for electrical laminate applications such as PWB.

Generally, laminates for use in the electronics industry, particularly for printed wiring boards, are produced by impregnating a reinforcing material with a polymer matrix, such as the thermosettable resin composition of the present invention, followed by the polymer matrix being cured wholly or in part.

For example, the curing reaction of the thermosettable composition may be conducted at a temperature, generally, between about 50° C. and about 250° C., preferably between about 80° C. and about 200° C., more preferably between about 100° C. and about 200° C. The time of curing the thermosettable resin composition may be for a predetermined period of time which can range from minutes up to hours, generally the reaction time is more than about 5 minutes and less than about 24 hours, preferably between about 30 minutes and about 6 hours, and more preferably between about 30 minutes and about 3 hours. The curing conditions of the thermosettable resin can also depend on the components used, and any optional components added to the composition such as a catalyst, if used. In other embodiments, curing may occur at a first temperature followed by a second temperature or post-treatment, such post-treatments ordinarily being at temperatures above 100° C., preferably between about 100° C. and 200° C.

In some embodiments, curing may be staged or "B-staged" to prevent uncontrolled exotherm. Staging, typically referred to as "B-staging", for example, includes curing for a period of time at a temperature followed by curing for a period of time at a higher temperature. B-staged curing may include two or more curing stages, and may commence at temperatures below about 180° C. in some embodiments, and below about 150° C. in other embodiments. A reinforcing material impregnated with a partially cured resin is usually referred to herein as the "prepreg". To make a printed wiring board from prepregs, one or more layers of prepregs are laminated with, for example, one or more layers of a metallic material such as copper.

Thermoset resins may be formed by curing the curable thermosettable resin compositions of the present invention as described above. The resulting thermoset resins of the present invention may comprise a thermoset or a thermoset network structure with fillers, fibrous reinforcement materials, aspect shaped inorganic materials and/or other additives. The term "thermoset" or "thermoset network structure" used herein refers to a fully cured and crosslinked thermoset resin structure.

The resulting composite or electrical laminate of the present invention displays excellent thermo-mechanical properties, such as good toughness and mechanical strength, while maintaining high thermal stability.

It has been discovered in the present invention that the dihydroxydiphenyl-cycloalkane compounds of the present invention provide several improved properties to the thermoset resins of the present invention when compared to conventional phenolic hardeners and/or chain extenders. For example, compared to conventional thermoset resins, the thermoset resins of the present invention comprising the dihydroxydiphenyl-cycloalkane compounds of the present invention have the following improved properties while maintaining its other properties such as high temperature stability and a high cross-linking density:

(1) an improved mechanical property such as improved toughness—based on difunctional resins with low crosslink density and therefore relatively tough;

(2) an improved thermal property such as a higher glass transition temperatures of greater than about 150° C., preferably greater than about 170° C., and more preferably greater than about 190° C. and above when cured with dicyandiamide;

(3) a higher humidity resistance property (a high moisture resistance or, in other words, a low water uptake);

(4) a lower dielectric constant/dissipation factor (Dk/Df) property; and (5) based on an epoxy resin that exhibits low viscosity of less than about 150 mPa-s and preferably less than about 120 mPa-s.

Without limiting the present invention to any one theory, it is theorized that the addition of the alkyl ring between the bisphenol groups in the dihydroxydiphenyl-cycloalkane structure may reduce the rotations of the bisphenol groups by steric hindrance and, as a result, the presence of the dihydroxydiphenyl-cycloalkane compound structure increases the glass transition temperatures (Tg) of the host resins compared to conventional resins which comprise bisphenol derivatives without the alkyl ring.

The increase of the glass transition temperatures of a host resin comprising the dihydroxydiphenyl-cycloalkane compounds of the present invention is generally in the range of from about 10° C. to about 100° C. or higher depending on factors such as type of hardener, resin, and catalyst used in curing the resins; and the curing conditions. The Young's moduli of a host resin comprising dihydroxydiphenyl-cycloalkane compounds is also found to be lower compared to resins comprising bisphenol derivatives without the alkyl ring. Thus, the compositions of the present invention exhibit a higher Tg. It is theorized, that the addition of the alkyl ring between the bisphenol groups in the dihydroxydiphenyl-cycloalkane compounds may lower the cross-linking density due to higher steric hinderance and thus, provides improved toughness to thermosettable resins such as epoxy resins.

EXAMPLES

The following examples and comparative examples further illustrate the present invention in detail but are not to be construed to limit the scope thereof.

Various terms and designations used in the following examples are explained herein as follows: D.E.R.™ 330 is a diglycidyl ether of bisphenol A having an epoxy equivalent weight (EEW) between 177 g/eq and 189 g/eq, available from The Dow Chemical Company; D.E.R.™ 560 is a diglycidyl ether of tetrabromobisphenol A with an EEW at about 455 g/eq, supplied by The Dow Chemical Company; Dowanol™ PM is a solvent containing propylene glycol methyl ether, supplied by The Dow Chemical Company; Plenco 13943 is a phenol novolac epoxy resin, available from Plastics Engineering Co.; "A1 catalyst" is a catalyst made of ethyltriphenylphosphonium acid acetate, available from Alfa Aesar; EPON™ P101 is a catalyst available from Hexion Chemical; "dicy" stands for dicyandiamide; "DMA" stands for Dynamic Mechanical Analysis; "DSC" stands for Differential Scanning calorimetry; "EEW" stands for epoxy equivalent weight; "HEW" stands for hydroxyl equivalent weight; "2-MI" stands for 2-methyl-imidazole; the suffix "A80" implies an acetone solution that has an 80 wt % solids concentration; "TBBA" stands for tetrabromobisphenol A, which has an equivalent weight of 272, supplied by The Dow Chemical Company; XZ92747 is bisphenol A novolac hardener having a bisphenol A content about 21% by weight, commercially available as KBE F4113 from Kolon Chemical (from Korea); XZ92755 is a bisphenol A novolac hardener based on KBE F4127 has lower bisphenol A content about 17% by weight, commercially available from Kolon Chemical (from Korea); and Herinol KBE F4127 is a bisphenol A novolac hardener based on KBE F4127 has lower bisphenol A content about 17% by weight, commercially available from Kolon Chemical (from Korea).

The following standard analytical equipments and methods are used in the Examples:

EEW was measured by a colorimetric titration of epoxy resin samples (about 0.4 mg) with 0.1 M perchloric acid in the presence of tetraethylammonium bromide in glacial acetic acid. Crystal violet was employed as indicator according to ASTM D 1652 method.

The glass transition temperature (Tg) was measured by Differential Scanning calorimetry (DSC) from 50° C. to 220° C. with a heating ramp of 20° C./minute.

The reactivity of a resin solution was measured by placing a sample of the resin solution on the surface of a hot plate at 170° C. The reactivity measurement of the resin solution is reported as elapsed time in second required for gelation ("gel time") at 170° C.

The softening point was determinate with a Mettler FP80 with a heating ramp of 3° C./minute from room temperature (about 25° C.) to 200° C.

Thermo-gravimetric Analysis (TGA) was used to measure the decomposition temperature Td. TGA was performed by using a thermo-gravimetric analyzer TGA2950 from TA Instruments which is fitted with an auto-sampling device and connected to a personal computer. TGA analyzer was operated under nitrogen atmosphere. The decomposition temperature Td was measured according to IPC-TM-650-2.3.40 with from 50° C. to 700° C. with a heating ramp of 10° C./minute. Td was determined at percent weight loss (except otherwise mentioned, i.e. 1%, 2%, 5%, or 10% weight loss). The typical experimental error was ±1° C.

Example 1

Advanced Reaction of Bisphenol Cyclododecanone with D.E.R.™ 330

A 66.8 grams (g) sample of bisphenol cyclododecanone (189.8 mmol) was dissolved in 133.1 grams of D.E.R.™ 330

(371.8 mmol) in a 500 ml glass reactor at 140° C. to form a mixture. The mixture was cooled to 80° C. and then 100 milligrams of an A1 catalyst solution (70% solids in methanol) was added to the mixture to start the reaction of the bisphenol cyclododecanone with D.E.R.™ 330. The advanced reaction was carried out at 150° C. to form Advanced Resin A. After 1 hour, the Advanced Resin A was characterized by titration. The EEW of the Advanced Resin A obtained from the titration was 520 g/eq ($EEW_{theory}$=551 g/eq). The Tg of the Advanced Resin A was measured by DSC with a heating ramp of 10° C./minute. The Tg was 54° C.

Comparative Example A

A 52.5 g sample of bisphenol A (230.3 mmol) was dissolved in 147.4 grams of D.E.R.™ 330 (411.7 mmol) in a 500 ml glass reactor at 140° C. The mixture was cooled to 80° C. and then 100 milligrams of an A1 catalyst solution (70% solids in methanol) was added to the mixture to start the advancement reaction of bisphenol A with D.E.R.™ 330. The reaction was carried out at 150° C. to form Comparative Advanced Resin A. After 1 hour, the Comparative Advanced Resin A was characterized by titration. The EEW of the Comparative Advanced Resin A obtained from the titration was 569 g/eq ($EEW_{theory}$=552 g/eq). The Tg of the Comparative Advanced Resin A was measured by DSC with a heating ramp of 10° C./minute. The Tg was 49° C.

The advanced bisphenol cyclododecanone resin (Example 1) has higher resin Tg than the advanced bisphenol A resin (Comparative Example A). A higher Tg for a resin can be beneficial to the resin's storage stability.

Example 2

Curing the Advanced Resin of Bisphenol Cyclododecanone and D.E.R.™ 330

A 20.0 g sample of the Advanced Resin A (EEW=520 g/eq) obtained from Example 1 above was mixed with 0.48 grams of dicy and 0.25 grams of EPON™ P101. The mixture was cured for 2 hours at 200° C. to form Cured Resin A. The Tg of the Cured Resin A was measured by DSC with a heating ramp of 10° C./minute. The Tg of Cured Resin A was 141° C.

Comparative Example B 20.0 grams of the Advanced Resin B (EEW=569 g/eq) obtained from Comparative Example A above was mixed with 0.45 grams of dicy (EEW=14 g/eq) and 0.26 grams of EPON P101.

The mixture was cured for 2 hour at 200° C. to form Cured Resin B. The Tg of Cured Resin B was measured by DSC with a heating ramp of 10° C./minute. The Tg of Cured Resin B was 115° C.

The cured resins of Example 2 and Comparative Example B show the Tgs for Cured Resin A (advanced bisphenol cyclododecanone resin, Example 2) and Cured Resin B (advanced bisphenol A resin, Comparative Example B) with a similar EEW. The use of the bisphenol cyclododecanone illustrates that Cured Resin A has an increased Tg over Cured Resin B of 26° C.

Example 3 and Comparative Example C

The toughness of two resins (Resin C and Comparative Resin C) was measured by DMA. The cured resin of Example 2 which comprises Resin C is an advanced bisphenol cyclododecanone resin prepared using the procedure in Example 1. Resin C was cured with Plenco 13943 using the procedure in Example 2. The cured resin is referred to herein as "Cured Resin C" (Example 3).

Comparative Resin C is a conventional bisphenol A, DER 330. Comparative Resin C was cured with Plenco 13943 [herein "Comparative Cured Resin C" (Comparative Example C)] using the procedure of Comparative Example B.

Cured Resin C and Comparative Cured Resin C have similar glass transition temperature (Tg) at about 130° C. The toughness of the above two resins can be compared because the resins have similar glass transition temperatures (Tg).

Toughness may be defined by a drop in Young's modulus (E'). The two resins get less stiff (modulus decreases) as a result of the glass transition at about 130° C. The Young's modulus (E') of Cured Resin C decreases from about $5 \times 10^9$ Pa before the Tg at 130° C. to about $3 \times 10^7$ Pa after the Tg at 130° C.

The Young's modulus (E') of Cured Resin C in the rubber modulus range (after Tg reaches 130° C.) has a lower Young's modulus (E') (improved toughness) than that of Comparative Cured Resin C in the same rubber modulus range. Accordingly, Cured Resin C has an improved toughness by using bisphenol cyclododecanone over Comparative Cured Resin C which uses a conventional bisphenol A.

The results of Examples of the present invention show that an epoxy resin comprising a diglycidyl ether of a dihydroxydiphenyl-cycloalkane compound has a higher resin glass transition temperature (resin Tg) than a conventional epoxy resin such as those based on bisphenol A (see Example 1 and Comparative Example A). The cured epoxy resin of the present invention shows a higher cured glass transition temperature (cured Tg) than an epoxy resin comprising a conventional epoxy resin based on bisphenol A (see Example 2 and Comparative Example B). The cured epoxy resin of the present invention also has improved mechanical properties such as toughness compared to a conventional epoxy resin cured by phenolic hardeners; and therefore, the epoxy resin of the present invention has improved resistance to impact (see Example 3 and Comparative Example C).

Example 4

Laminates Produced from Advanced Bisphenol Cyclododecanone Resin

Part A. Advanced Bisphenol Cyclododecanone with D.E.R.™ 330

A 99.88 g sample of bisphenol cyclododecanone (0.57 mol) was solved in 399.88 grams of D.E.R.™ 330 (2.22 mol) in a 500 ml glass reactor at 140° C. to form a mixture. The mixture was cooled to 80° C. and then 231 mg of an A1 catalyst solution (70% solids in methanol) was added to the mixture. The resulting mixture with the A1 catalyst solution was heated to about 150° C. An advanced reaction of the bisphenol cyclododecanone and the D.E.R.™ 330 was carried out at 150° C. for about 1 hour to form an Advanced Resin E.

The EEW of the Advanced Resin E, measured by titration, was 297 g/eq ($EEW_{theory}$ is 302 g/eq). The Tg of the Advanced Resin E, measured by DSC, was 13° C.

75.0 grams of the Advanced Resin E (EEW=297 g/eq) obtained from the above reaction and 29.5 grams of Herinol KBE F4127 (HEW=117) was solved in 75.0 g Dowanol™ PM to form a Resin F. The reactivity (i.e. gel time in second)

of the Resin F was adjusted to 280 second by adding 400 mg of the 2-MI solution (20% solids in Dowanol™ PM).

Part B. Prepregs and Laminates

Prepregs were prepared by coating 47% by weight of Resin F prepared in Part A above (calculated without solvent, i.e. with 100% solid content) on 53% by weight of style 7628 glass cloth (Porcher 73I finish). The solvent (Dowanol™ PM) in Resin F was evaporated in an oven which temperature was set at about 165° C. for about 5 minutes to form the prepregs.

The prepregs prepared above were used to produce laminates without any further modifications as follows: 8 sheets (each 20 cm×20 cm) of the prepregs were pressed for 1 hour at about 190° C. in a flow press with pressure at about 0.7 bar to form the laminates.

Example 5

Brominated Advanced Bisphenol Cyclododecanone Resin

A mixture of 150 grams (based on 100% solid content) of bisphenol cyclododecanone, 150 grams of D.E.R.™ 560 (based on 100% solid content with 58.8% Br), and 200 grams of Dowanol™ PM solvent was charged in a reactor. The mixture was warmed up to 60° C. to dissolve the bisphenol cyclododecanone and the D.E.R.™ 560 in the Dowanol™ PM solvent. The mixture was then heated up to 100° C. with 0.643 grams of A1 catalyst solution (70% solids in methanol) added to the mixture. The mixture was heated continuously until the Dowanol™ PM solvent started to boil at reflux (137° C.). The advanced reaction of the bisphenol cyclododecanone and the D.E.R.™ 560 was carried out at 137° C. for about 150 minutes to form a brominated Advanced Resin G. The brominated Advanced Resin G was cooled down to room temperature.

The EEW and the Tg of the brominated Advanced Resin G were measured according to the methods stated above. The results are listed as follows: the EEW was 297 g/eq (EEW$_{theo}$ is 302 g/eq) and the Tg was 13° C.

The brominated Advanced Resin G was used to form a resin formulation with hardeners, XZ92747 and XZ92755, available from The Dow Chemical Company.

About 59.95% by weight of the brominated Advanced Resin G obtained from the above reaction and 33.29% by weight of XZ92747 and 6.63% by weight of XZ92755 were solved in 0.13% by weight of 2-MI solution (20% solids in Dowanol™ PM) to form a resin formulation.

The reactivity of the resin formulation was measured three times with an average result of 249 seconds. The Tg were measured by DSC (film) by scanning two times from 50° C. to 220° C. at 20° C./minute with an average result of 120° C. The resin formulation was subsequently cured on a hot plate at 170° C. for 10 minutes and 190° C. for 90 minutes to form a cured brominated advanced bisphenol cyclododecanone resin product.

Example 6

Formation of an Epoxidized Bisphenol Cyclododecanone (Bisphenol Cyclododecanone Modified Epoxy Resin)

Epoxidation of bisphenol cyclododecanone was carried out by reacting the bisphenol cyclododecanone with epichlorohydrin with a ratio of 7.5:1 (epichlorohydrin to hydroxyl (—OH) equivalent) according to the following procedure:

A two liter, three necks, round bottom glass reactor equipped with a thermostatically controlled heating mantle was charged with the bisphenol cyclododecanone (176 g, 1.0 hydroxyl equivalent), epichlorohydrin (694 g, 7.5 moles) and isopropanol (373 g, 35% weight of the epichlorohydrin used). The reactor was maintained at 50° C. during the experiment. The reactor was additionally equipped with a condenser (maintained at −15° C.), a thermometer, a Claisen adaptor, an overhead nitrogen inlet (1 LPM N$_2$ used), and a stirrer assembly (PTFE paddle, glass shaft, variable speed motor). An initial sodium hydroxide solution (20% in water, 180 grams) was added from a side arm vented addition funnel over 20-30 minutes. The resulting mixture was stirred to give a slurry of the bisphenol cyclododecanone in the epichlorohydrin and isopropanol.

After 20 minutes of post-reaction, stirring was stopped. An aqueous layer and an organic layer were formed. The aqueous layer was removed from the mixture. Heating and stirring of the organic layer were resumed to 50° C. Dropwise addition of a second portion of sodium hydroxide (20% in water, 80 grams) was completed over 20 minutes while maintaining the temperature at 50° C.

Similarly, after 20 minutes of post-reaction, stirring was stopped; and an aqueous layer and an organic layer were formed. The aqueous layer was removed from the mixture. The organic layer was washed with 3-4 portions (250 milliliters each) of deionized water until a pH of 7 of the organic layer was achieved. Rotary evaporation of the organic layer using a maximum oil bath temperature of 75° C. was used to remove the bulk of volatiles presence in the organic layer. Further rotary evaporation at 125° C. for 2-3 hour (16 mbar) gave 230 grams of epoxidized bisphenol cyclododecanone, which was a transparent, colorless liquid. The resulting liquid was solidified to a brittle solid at room temperature (about 25° C.).

Example 7

Advanced Brominated Epoxy Resin Formed by Advanced Reaction of Epoxidized Bisphenol Cyclododecanone and TBBA A 7.63 g sample of an epoxidized bisphenol cyclododecanone product (EEW 236 g/eq) obtained from Example 6 above and 4.52 grams of TBBA (EEW 272 g/eq, 58.8% Br) were molten in an aluminum cup on a hot plate to obtain a homogenous mixture. About 0.0049 grams of A1 catalyst was added to the homogeneous mixture. An advanced reaction of the epoxidized bisphenol cyclododecanone product and TBBA was carried out at 120° C. for 1 hour to form an advanced resin. The advanced resin was then dissolved in 2.98 grams of acetone (80% solids in acetone) with dicy to form a resin mixture. The resin mixture was cured on a hot plate at 170° C. for 10 minutes and 190° C. for 90 minutes to form an advanced brominated epoxy resin product.

The reactivity of the advanced brominated epoxy resin was measured three times. The resin had an average reactivity of 205 seconds. The Tg of the resin was measured by DSC (film). The film was scanned 2 times from 50° C. to 220° C. at 20° C./minute. The resin had an average Tg of 168.3° C. Film decomposition temperature (Td) of the brominated epoxy resin was measured by TGA according to the procedure stated above. The results of the Td measurements are shown in the following Table I.

TABLE I

| Weight Loss (%) | Film (Td) Temperature (° C.) |
|---|---|
| 1 | 210.7 |
| 2 | 250.0 |
| 5 | 297.7 |
| 10 | 300.9 |

Example 8 and Comparative Example D

Part A. Prepreg Procedure

Prepregs were prepared by impregnating glass web (Porcher style Nr.7628136 amine silane finish) with a varnish mixture. One varnish mixture (Example 8) was made from the advanced brominated resin of Example 7; and another varnish mixture (Comparative Example D) a conventional epoxidized bisphenol A advanced with TBBA. The prepregs were formed using a Caratsch pilot treater 3 meters in length. The "Hand Lay-ups" were prepared by pouring the varnish onto the glass web. The varnish was spread across the glass web before the glass web was passed through the treater rollers. The resin impregnated web was then passed through the treater; and heated at a temperature of between 175-180° C. to form the resulting prepreg.

Part B. Laminate Procedure

A laminate was prepared using 8 plies of prepregs from Part A above and copper foil on the top and bottom. The 8 plies were pressed at 20 N/cm² from room temperature to 190° C. with a heating ramp of 3° K/min and kept 90 minutes.

The following Table II shows a comparison of the properties of laminates made from a conventional epoxidized bisphenol A advanced with TBBA (Comparative Example D) and laminates made from an epoxidized bisphenol cyclododecanone product of Example 7 advanced with TBBA (Example 8).

TABLE II

|  | Comparative Example D | Example 8 |
|---|---|---|
| Formulation |  |  |
|  | Epoxidized Bisphenol A Advanced with TBBA | Epoxidized Bisphenol Cyclododecanone Advanced with TBBA |
| Parts Solid | 100 | 100 |
| dicy | 2.8 | 3.0 |
| 2-MI | 0.08 | 0.10 |
| Laminate Properties: |  |  |
| Glass Transition Temperature Tg (° C.) | 130-140 | 167-169 |
| Decomposition Temperature Td (° C.) | 315 | 298 |

Example 9

Synthesis of Epoxidized Bisphenol Cyclododecanone

A two liter, three necks, round bottom glass reactor equipped with a thermostatically controlled heating mantle was charged with the bisphenol of cyclododecanone (~176 grams, 1.0 hydroxyl equivalent), epichlorohydrin (~694 grams, 7.5 moles) and isopropanol (~373 grams, 35% weight of the epichlorohydrin used). The reactor was additionally equipped with a condenser (maintained at −15° C.), a thermometer, a Claisen adaptor, an overhead nitrogen inlet (1 LPM N₂ used), and a stirrer assembly (Teflon paddle, glass shaft, variable speed motor). After dissolving at 50° C., a solution of sodium hydroxide (20% in water, 180 grams) was added to a side arm vented addition funnel over 20-30 minutes. Stirring commenced to give slurry of the bisphenol of cyclododecanone in epichlorohydrin and isopropanol. The temperature was maintained at 50° C. during the reaction. After 20 minutes of post-reaction, stirring was stopped and the aqueous layer was removed from the organic layer.

Heating and stirring of the organic layer was resumed to 50° C. Dropwise addition of a second portion of sodium hydroxide (20% in water, 80 grams) to the organic layer was completed over 20 minutes while maintaining the temperature at 50° C. After 20 minutes of post-reaction, stirring was stopped, and the aqueous layer was removed from the organic layer product. Then the organic layer was washed with 3-4 portions (250 milliliters each) of deionized water until a pH of 7 of the organic layer was achieved.

Rotary evaporation of the organic layer using an oil bath temperature of 75° C. was used to remove the bulk of the volatiles. Further rotary evaporation at 125° C. for 2-3 hour (16 mbar) gave ~225-235 grams of transparent, colorless liquid which solidified to a brittle solid at room temperature (~25° C.). The resulting resin was the diglycidyl ether of bisphenol cyclododecanone (herein "eCDON") and had the following properties as described in Table III:

TABLE III

| Example 1 Resin | Tg (° C.)[1] | Softening Point (° C.)[2] | Melt viscosity at 150° C. (mPa-s) | EEW measured by titration (g/eq) |
|---|---|---|---|---|
| eCDON | 31 | 74.6 | 120 | 236 |

[1]Midpoint of DSC transition at a 10° C./minute ramp rate
[2]Ramp rate 2° C./minute

Example 10

Cure of eCDON with Dicy

A sample of eCDON (4.62 g), dicy (0.34 g), and 2-phenylimidazole (0.038 g) was mixed by cryogrinding. This procedure involves adding the solids to a stainless steel cylinder with threaded ends, adding a metal ball, cooling the contents in liquid nitrogen, and shaking the assembly for 10 minutes. The cylinder was placed in a nitrogen-purged bag and allowed to warm to room temperature. A portion of the powder was placed in an aluminum pan, and heated in a vacuum oven at 190° C. for 90 minutes to form a clear casting. A Tg of 202° C. was observed by DSC. This casting was cut into 4 pieces, each was weighed, and all were placed in a steam autoclave at 121° C. for 90 minutes. The weight gain of each piece was expressed as a percentage, and the 4 values were averaged to give a value of 2.3 wt %.

Comparative Example E

Cure of D.E.R.™ 331 with Dicy

The experiment described in Example 10 was repeated using D.E.R.™ 331 (bisphenol A diglycidyl ether, 4.51 g), dicy (0.44 g), and 2-phenylimidazole (0.05 g). A Tg of 139° C. was observed by DSC, and the water absorption was 3.9 wt %.

What is claimed is:

1. A curable resin composition for composites and electrical laminates comprising (I) at least one thermoset resin composition; (II) at least one hardener; and (III) at least one reinforcing material;

wherein the thermoset resin composition comprises an advanced epoxy resin composition represented by the following general Formula II:

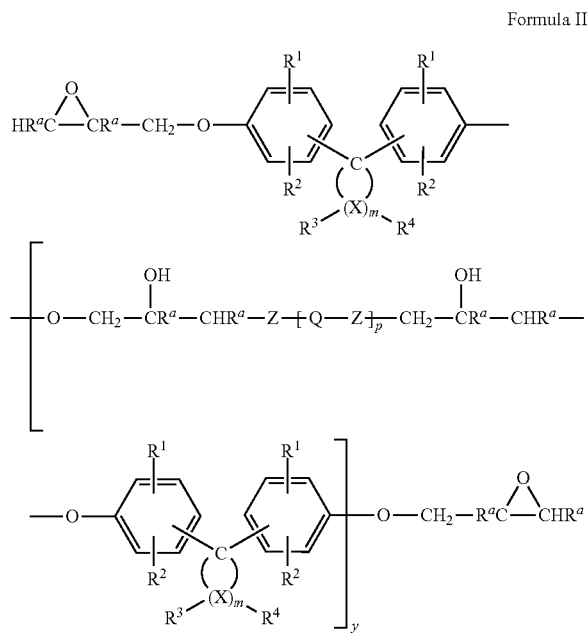

Formula II wherein $R^a$ is a hydrogen or methyl group, $R^1$ and $R^2$, independently from each other, each represents a hydrogen atom, a halogen, a substituted or unsubstituted alkyl group, a substituted or unsubstituted aryl group, or a substituted or unsubstituted aralkyl group; a nitrile group; a nitro group; a substituted or unsubstituted alkoxy group; X is $CH_2$, $CH(R^3)$, or $C(R^3)(R^4)$; m is an integral number between 8 and 20; $R^3$ and $R^4$, independently from each other, each represents a hydrogen atom, a halogen, a substituted or unsubstituted alkyl group, a substituted or unsubstituted aryl group, or a substituted or unsubstituted aralkyl group; p and y are integers having a value from 1 to about 20; Q is a hydrocarbylene moiety, and each Z is independently selected from the group consisting of O, S, $-NR^b$, wherein $R^b$ is a hydrocarbyl moiety.

2. The composition of claim 1, wherein the reinforcing material comprise high strength filaments or fibers.

3. The composition of claim 1, wherein the at least one thermoset resin composition further comprises a thermosetting resin component selected from the group consisting of epoxy resins, isocyanate resins, (meth)acrylic resins, phenolic resins, vinylic resins, styrenic resins, polyester resins, and mixtures thereof.

4. The composition of claim 1, further comprising at least one of: (IV) an epoxy resin different from Formula I; (V) a filler; (VI) a flame retardant; (VII) a catalyst; and (VIII) a solvent.

5. The composition of claim 1, wherein component (I) comprises from about 20 percent by weight to about 98 percent by weight based on total weight of the composition; and wherein component (II) comprises from about 2 percent by weight to about 50 percent by weight based on total weight of the composition.

6. A composite or a laminate article made from the composition of claim 1.

7. The article of claim 6, wherein the article is a printed wiring board, an electrical or electronic casting, an electrical or electronic potting, an electrical or electronic encapsulation, or an electrical laminate.

8. A curable resin composition for composites and electrical laminates comprising (I) at least one thermoset resin composition; (II) at least one hardener; and (III) at least one reinforcing material;

wherein the thermoset resin composition comprises an advanced active hydrogen-functional resin composition represented by the following general Formula III:

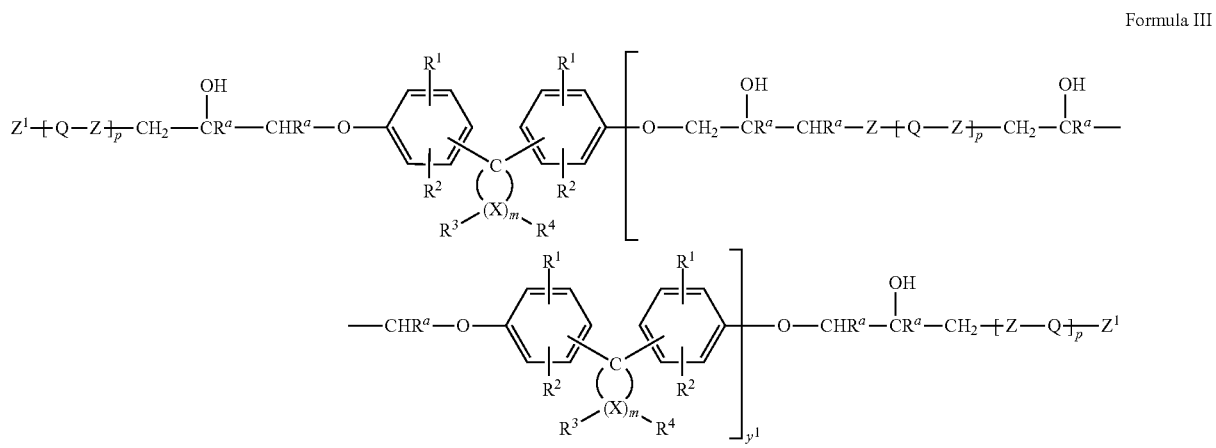

Formula III wherein $R^a$ is a hydrogen or methyl group, $R^1$ and $R^2$, independently from each other, each represents a hydrogen atom, a halogen, a substituted or unsubstituted alkyl group, a substituted or unsubstituted aryl group, or a substituted or unsubstituted aralkyl group; a nitrile group; a nitro group; a substituted or unsubstituted alkoxy group; X is CH$_2$, CH(R$^3$), or C(R$^3$)(R$^4$); m is an integral number between 8 and 20; R$^3$ and R$^4$, independently from each other, each represents a hydrogen atom, a halogen, a substituted or unsubstituted alkyl group, a substituted or unsubstituted aryl group, or a substituted or unsubstituted aralkyl group; and n is an integer having a value from 0 to about 10, Q is a hydrocarbylene moiety, Z is independently selected from the group consisting of O, S, —NR$^b$, wherein R$^b$ is a hydrocarbyl moiety; and p is an integer having a value from 1 to about 20; y$^1$ is an integer having a value from 0 to about 20; and Z$^1$ is Z—H.

9. The composition of claim 8, wherein the reinforcing material comprise high strength filaments or fibers.

10. The composition of claim 8, wherein the at least one thermoset resin composition further comprises a thermosetting resin component selected from the group consisting of epoxy resins, isocyanate resins, (meth)acrylic resins, phenolic resins, vinylic resins, styrenic resins, polyester resins, and mixtures thereof.

11. The composition of claim 8, further comprising at least one of: (IV) an epoxy resin different from Formula I; (V) a filler; (VI) a flame retardant; (VII) a catalyst; and (VIII) a solvent.

12. The composition of claim 8, wherein component (I) comprises from about 20 percent by weight to about 98 percent by weight based on total weight of the composition; and wherein component (II) comprises from about 2 percent by weight to about 50 percent by weight based on total weight of the composition.

13. A composite or a laminate article made from the composition of claim 8.

14. A curable resin composition for composites and electrical laminates comprising (I) at least one thermoset resin composition; (II) at least one hardener; and (III) at least one reinforcing material;
wherein the at least one thermoset resin of component (I) comprises a diglycidyl ether of a dihydroxydiphenyl-cycloalkane compound; and wherein the dihydroxydiphenyl-cycloalkane compound comprises a dihydroxydiphenyl-cycloalkane compound represented by the following general Formula IV:

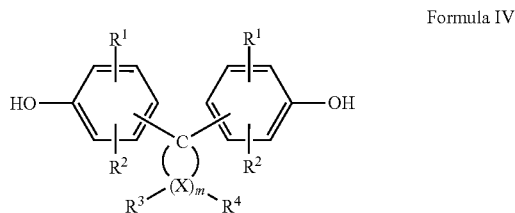

Formula IV wherein R$^1$ and R$^2$, independently from each other, each represents a hydrogen atom, a halogen, a substituted or unsubstituted alkyl group, a substituted or unsubstituted aryl group, or a substituted or unsubstituted aralkyl group; X is CH$_2$, CH(R$^3$), or C(R$^3$)(R$^4$); m is an integral number between 8 and 20; and R$^3$ and R$^4$, independently from each other, each represents a hydrogen atom, a halogen, a substituted or unsubstituted alkyl group, a substituted or unsubstituted aryl group, or a substituted or unsubstituted aralkyl group.

15. The composition of claim 14, wherein the dihydroxydiphenyl-cycloalkane compound is made from a cycloalkane compound containing from about C8 to about C20 carbon atoms.

16. The composition of claim 15, wherein the cycloalkane compound is selected from the group consisting of cyclooctanone, cyclodecanone, cyclododecanone, cyclopentadecanone, cyclooctadecanone, cycloeicosanone, and mixtures thereof.

17. The composition of claim 16, wherein cycloalkane compound comprises a bisphenol cyclododecanone.

* * * * *